United States Patent
Madabhushi et al.

(10) Patent No.: US 10,441,225 B2
(45) Date of Patent: Oct. 15, 2019

(54) PREDICTING DISEASE RECURRENCE FOLLOWING TRIMODALITY THERAPY IN NON-SMALL CELL LUNG CANCER USING COMPUTED TOMOGRAPHY DERIVED RADIOMIC FEATURES AND CLINICO-PATHOLOGIC FEATURES

(71) Applicant: Case Western Reserve University, Cleveland, OH (US)

(72) Inventors: Anant Madabhushi, Shaker Heights, OH (US); Mohammadhadi Khorrami, Cleveland, OH (US); Vamsidhar Velcheti, Pepper Pike, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 16/236,675

(22) Filed: Dec. 31, 2018

(65) Prior Publication Data

US 2019/0254611 A1   Aug. 22, 2019

Related U.S. Application Data

(60) Provisional application No. 62/633,411, filed on Feb. 21, 2018.

(51) Int. Cl.
*A61B 5/00* (2006.01)
*G06T 7/00* (2017.01)
(Continued)

(52) U.S. Cl.
CPC .......... *A61B 5/7267* (2013.01); *G06K 9/6284* (2013.01); *G06T 7/0016* (2013.01);
(Continued)

(58) Field of Classification Search
CPC ........ G06T 7/11; G06T 7/155; G06T 7/0016; G06K 9/6284
See application file for complete search history.

(56) References Cited

U.S. PATENT DOCUMENTS

| 2014/0321615 | A1* | 10/2014 | Carlsson | A61N 5/1049 378/62 |
| 2017/0071496 | A1* | 3/2017 | Gillies | G01R 33/5602 |
| 2018/0360402 | A1* | 12/2018 | Carmi | G06T 7/13 |

* cited by examiner

Primary Examiner — Edward Park
(74) Attorney, Agent, or Firm — Eschweiler & Potashnik, LLC

(57) ABSTRACT

Embodiments include operations, apparatus, methods and other embodiments that access a baseline CT image of a region of tissue (ROT) demonstrating non-small cell lung cancer (NSCLC), segment a tumoral region represented in the baseline CT image; define a peritumoral region by dilating the tumoral boundary; extract a set of tumoral radiomic features from the tumoral region, a set of peritumoral radiomic features from the peritumoral region, and a set of clinico-pathologic features from the baseline CT image; provide the set of tumoral radiomic features, peritumoral radiomic features, and clinico-pathologic features to a machine learning classifier; receive, from the machine learning classifier, a time-to-recurrence post trimodality therapy (TMT) prediction, based on the set of tumoral radiomic features, peritumoral radiomic features, and clinico-pathologic features; generate a classification of the ROT as an MPR responder or MPR non-responder based, at least in part, on the time-to-recurrence post-TMT prediction; and display the classification.

20 Claims, 12 Drawing Sheets

(51) Int. Cl.
*G06T 7/11* (2017.01)
*G06T 7/155* (2017.01)
*G06K 9/62* (2006.01)

(52) U.S. Cl.
CPC ............... *G06T 7/11* (2017.01); *G06T 7/155* (2017.01); *G06T 2207/10081* (2013.01); *G06T 2207/20081* (2013.01); *G06T 2207/30061* (2013.01); *G06T 2207/30096* (2013.01)

| MRMR feature selection method | | | | | |
|---|---|---|---|---|---|
| Feature Family | Descriptor | Statistic | Location | p-value (training) Reader 1 | p-value (training) Reader 2 |
| 1 Law_Laplacian | S5 × R5 | Skewness | Peritumoral | 0.0289 | 0.0481 |
| 2 Law | W5 × S5 | Kurtosis | Peritumoral | 0.0475 | 0.0337 |
| 3 Law | E5 × W5 | Kurtosis | Intratumoral | 0.0313 | 0.0293 |
| 4 Gabor | f = 8, θ = 0 | SD | Intratumoral | 0.0304 | 0.0446 |
| 5 Shape | Area | Mean | Peritumoral | 0.0291 | 0.0238 |
| 6 Law_Laplacian | W5 × S5 | Var | Peritumoral | 0.0209 | 0.0199 |
| 7 Gabor | f = 8, θ = 0 | Median | Intratumoral | 0.05 | 0.058 |
| 8 Law_Laplacian | E5 × W5 | Kurtosis | Intratumoral | 0.0403 | 0.0289 |
| 9 Haralick | Inertia | SD | Intratumoral | 0.0755 | 0.1803 |
| 10 Law_Laplacian | E5 × W5 | Skewness | Intratumoral | 0.05 | 0.0423 |
| 11 Law_Laplacian | W5 × E5 | Var | Intratumoral | 0.0430 | 0.0477 |
| 12 Gabor | f = 16, θ = 0 | SD | Intratumoral | 0.0384 | 0.0455 |
| 13 Gabor 148 | f = 8, θ = 0 | Skewness | Intratumoral | 0.0831 | 0.0779 |

Figure 5

PREDICTING DISEASE RECURRENCE FOLLOWING TRIMODALITY THERAPY IN NON-SMALL CELL LUNG CANCER USING COMPUTED TOMOGRAPHY DERIVED RADIOMIC FEATURES AND CLINICO-PATHOLOGIC FEATURES

CROSS REFERENCE TO RELATED APPLICATIONS

This application claims the benefit of U.S. Provisional Application 62/633,411 filed Feb. 21, 2018, which is incorporated by reference herein in its entirety.

FEDERAL FUNDING NOTICE

This invention was made with government support under grants 1U24CA199374-01, R01 CA202752-01 A1, R01 CA208236-01 A1, R21 CA216579-01 A1, R21CA195152-01, R01DK098503-02, and 1 C06 RR012463-01 awarded by the National Institutes of Health. Also grants W81XWH-13-1-0418 and W81XWH-14-1-0323, W81XWH-16-1-0329 awarded by the Department of Defense. The government has certain rights in the invention.

BACKGROUND

Tumoral heterogeneity is associated with more aggressive tumor phenotype and poor clinical outcome. Stage III non-small cell lung cancer (NSCLC) is a heterogeneous disease. The treatment of stage III NSCLC involves a multi-disciplinary approach and careful patient selection to determine which resectable patients might benefit from trimodality therapy (TMT). TMT includes neoadjuvant chemotherapy (NAC) followed by surgery. NAC administered prior to surgery can reduce tumor extent and metastases, thereby improving resectability. The role of surgery in stage IIIA patients is, however, controversial. Survival benefit of surgery in this setting has been difficult to demonstrate in multi-institute trials compared to definitive chemoradiation. The effectiveness of TMT is variable. Major pathologic response (MPR), defined as <=10% residual tumor, is strongly associated with improved overall survival (OS) following NAC. However, there are no clinically validated biomarkers to predict MPR. Existing patient selection approaches are based on anatomic and physiologic criteria. For example, in existing clinical practice, the selection of patients for TMT is based on relatively limited lymph node burden, single lobe involvement, and patient fitness, with little or no attention paid to specific markers of response. Thus, existing approaches suffer from low accuracy, intra-observer variability, as well as inter-observer variability, and are sub-optimal.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

FIG. 5 is a table of radiomic features selected using a feature selection approach.

DETAILED DESCRIPTION

Figure 1:
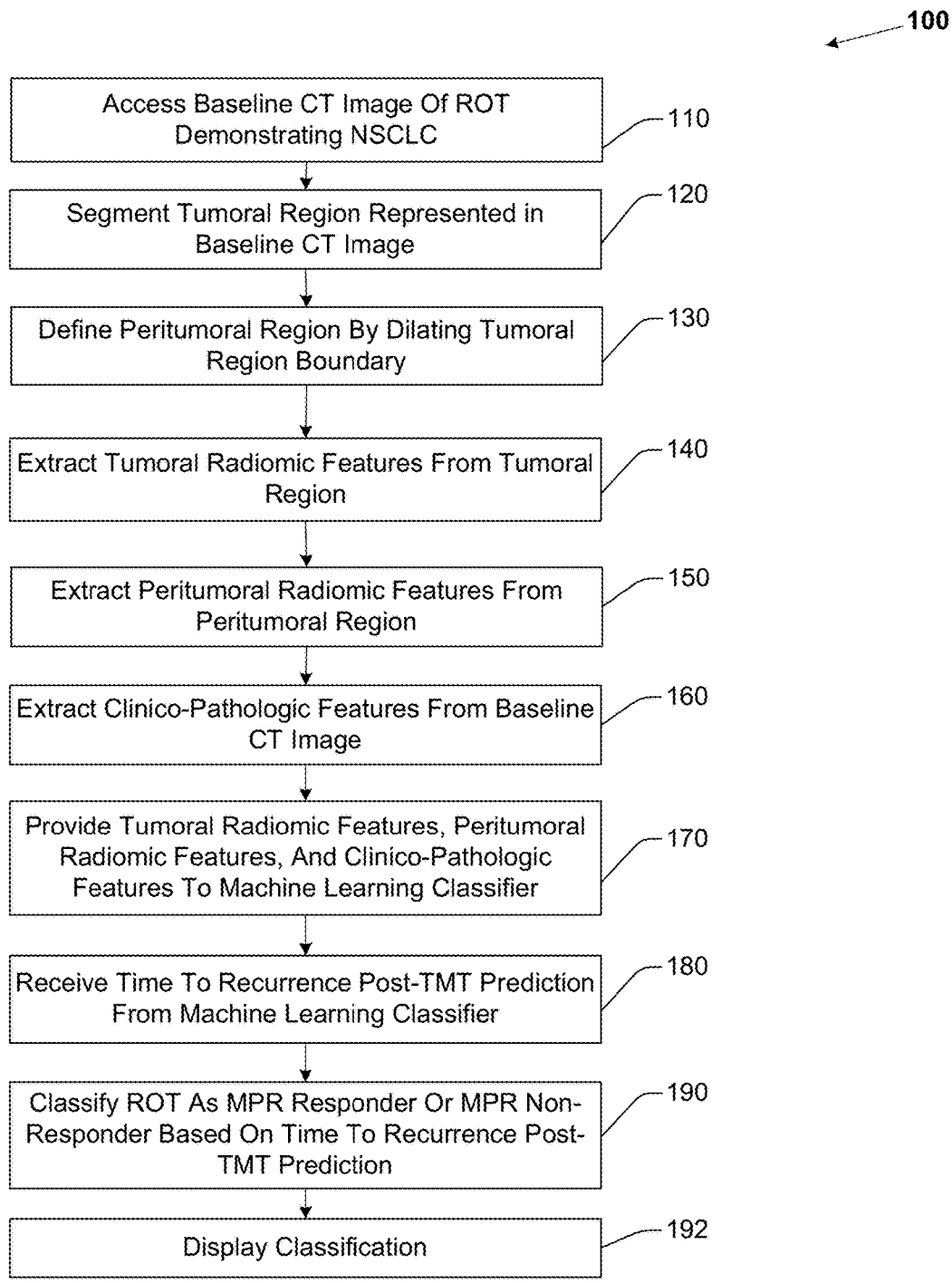
FIG. 1 is a flow diagram of example operations for predicting MPR in NSCLC.

The use of neoadjuvant chemotherapy (NAC) followed by surgery in patients with stage IIIA NSCLC is controversial, and the benefit of surgery is limited. There are currently no clinically validated biomarkers to select patients for TMT. Pathologic response to chemoradiation is highly predictive of disease free survival and overall survival. MPR is defined as <=10% residual tumor. The degree of down staging correlates with survival, with the greatest benefit associated with MPR noted on resected specimens. However, there are no existing clinically validated and approved biomarkers to predict MPR to chemoradiation. Radiomics (e.g., computerized feature extraction and analysis of radiographic imagery) that capture quantitative phenotypic attributes of NSCLC tumors may be employed to predict survival. Existing approaches to predicting response to first-line chemotherapy and neoadjuvant chemoradiation in patients with NSCLC capture and associate quantitative measurements of intratumoral heterogeneity and tumor shape from computed tomography (CT) imagery. Thus there is an unmet technical need for more accurate, more reproducible, prediction of MPR in NSCLC patients.

Embodiments identify NSCLC patients, including stage IIIA NSCLC patients, for aggressive TMT based on radiomic features and lymphovascular invasion (LVI) status extracted from baseline (i.e., pre-chemotherapy, pre-surgery) CT imagery. Embodiments predict MPR in stage IIIA NSCLC patients following chemoradiation, where MPR is used to define patient outcome (e.g., MPR, non-MPR). Embodiments extract quantitative radiomic features related to tumor shape and texture from intratumoral and peritumoral regions from baseline CT imagery. Embodiments may further extract clinico-pathologic features, including LVI status, from the intratumoral and peritumoral regions.

Embodiments provide the radiomic features and clinico-pathologic features to a machine learning classifier which distinguishes patients as likely to experience MPR following TMT or unlikely to experience MPR following TMT. The machine learning classifier may distinguish patients based, at least in part, on a prediction of time to recurrence post TMT. Embodiments may then identify a patient as a candidate who will likely benefit from TMT. Embodiments may further generate a prediction of overall survival (OS) or distinguish patients based on time to recurrence (TTR) post-TMT based on the radiomic features and clinico-pathologic features. Embodiments may determine which radiomic features or clinico-pathologic features are most discriminative and stable in predicting MPR following TMT. Embodiments may further train the machine learning classifier with the radiomic features, the clinico-pathologic features, or a subset of the radiomic features or clinico-pathologic features.

One embodiment includes controlling a processor to access a digitized baseline non-contrast CT image of a region of tissue demonstrating stage IIIA NSCLC. The digitized baseline CT image includes a plurality of pixels, a pixel having an intensity. The digitized baseline CT image includes a representation of a tumor, including a tumoral region and a peritumoral region. The peritumoral region is defined by a morphological operation applied to the tumoral boundary. For example, the peritumoral region may be defined by dilating the tumoral boundary. In this embodiment, radiomic features are extracted from the tumoral region and from the peritumoral region, including Laplacian Laws features that capture micro-gradients and patterns of heterogeneous enhancement from the baseline CT image. In this embodiment, LVI signature status is also extracted from the baseline CT image. The extracted radiomic features and the LVI signature status are provided to a machine learning classifier. For example, in one embodiment, a radiomic risk-score is generated by a linear combination of five radiomic texture features and three clinicopathologic measurements (e.g., histology, lymphatic invasion, and percentage of viable tumor). A Cox regression analysis computes risk-score as an independent risk factor for DFS (HR: 2.72, 95% CI: 1.73-4.27, p-value=1.4e-05). In this embodiment, a patient is stratified into a high risk group or a low risk group based on the median of radiomic risk-score signature (testing set: p-value=7.3e-08). For example, a patient having a risk-score above the median may be classified into the high risk group, and a patient having a risk-score below the median may be classified into the low risk group. Other classification schemes may be employed.

Embodiments may train the machine learning classifier. In one embodiment, the machine learning classifier is a support vector machine (SVM). The SVM is trained using three-fold cross validation with radiomic features and clinicopathologic features on a training set of baseline non-contrast CT images that include a region of tissue demonstrating stage IIIA NSCLC.

In one embodiment, the training set include images acquired of forty-five (45) patients demonstrating stage IIIA NSCLC, randomly selected from among ninety (90) patients demonstrating stage IIIA NSCLC, where pathological response was achieved in 36 of the 90 patients, and 54 patients were non-responders to TMT. The remaining 45 patients were allocated to a validation set. Radiomic texture and shape features were extracted from the intra-tumoral region and from the parenchymal regions immediately surrounding the nodule in the peritumoral region. In this embodiment, a total of thirteen stable and predictive intra-tumoral and peritumoral radiomic texture features predictive of MPR were identified using a feature selection approach. A univariate regression analysis was performed on the texture and clinic-pathologic features, and features with p-value<0.05 were included into a multivariable logistic regression (MLR) for binary outcome prediction of MPR. The MLR classifier yielded an area under the receiver operating characteristic curve (AUC) of at least 0.92±0.045 within the training set and a corresponding AUC of at least 0.88 for the patients within the test set.

Figure 3:
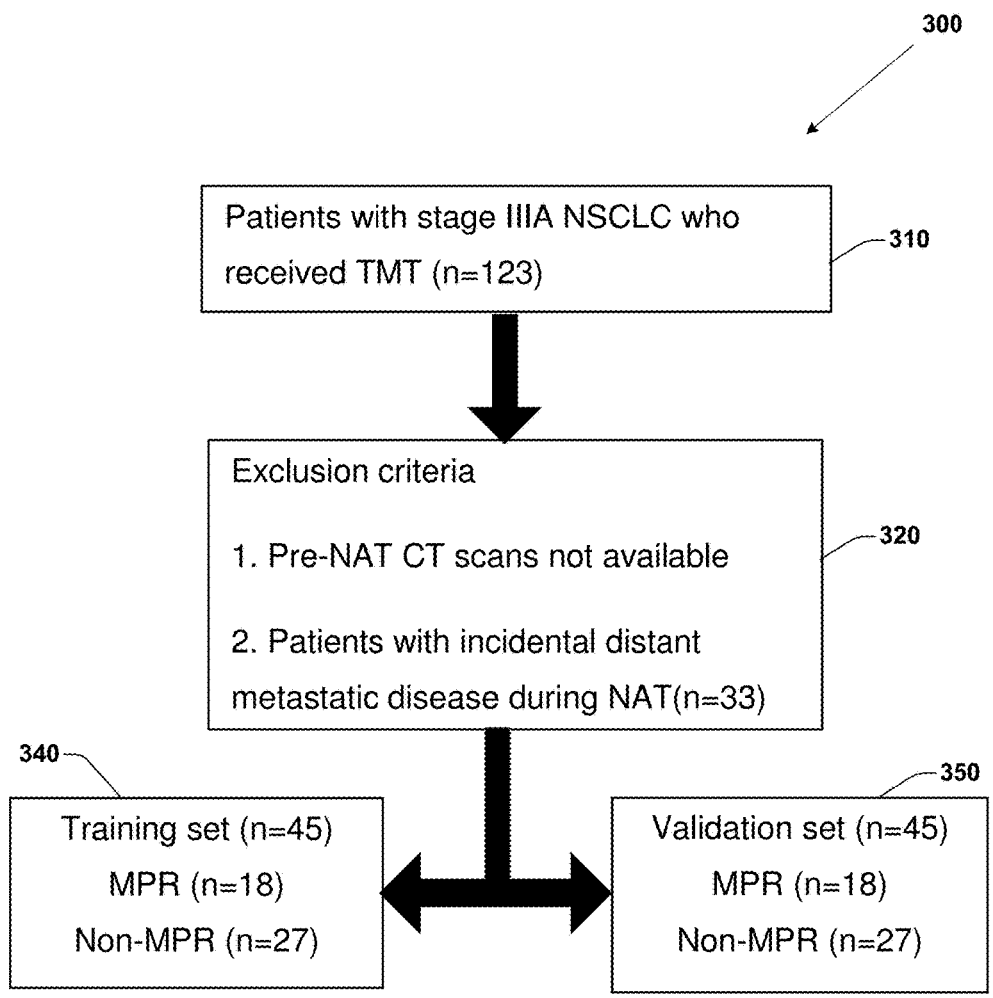
FIG. 3 illustrates a workflow for selecting a training set and a validation set for training a machine learning classifier to predict MPR.

FIG. 3 illustrates a workflow 300 for selecting patients from among a set of candidate patients for inclusion or exclusion from the training set or the validation set according to embodiments. At 310, patients with stage IIIA NSCLC who received TMT are considered for inclusion. In one embodiment, 123 patients (n=123) were considered. At 320, exclusion criteria are applied to the set of patients. In this embodiment, patients for whom pre-NAC CT images are not available are excluded. Also in this embodiment, patients who experienced incidental metastatic disease during NAC (n=33) were excluded. Remaining patients are, in this embodiment, divided equally into the training set at 340, or the validation set at 350. In each of the training set and the validation set, 18 patients experienced MPR (MPR responder), while 27 did not experience MPR (MPR non-responder). In other embodiments, other workflows, exclusion criteria, training set size, or validation set size, may be employed for selecting patients and corresponding CT imagery for the training set or validation set.

Embodiments predict major pathological response, defined as ≤10% of residual viable tumor, assessed at the time of surgery. Patients who had MPR were classified as 'responders' and those who did not have MPR were classified as non-responders. The secondary endpoints were OS and disease-free survival (DFS). OS is measured from the date of surgery to the date of death and censored at the date of last follow-up for survivors. DFS is measured from the date of surgery to the date of recurrence or the date of death, whichever occurs earlier, and censored at the date of last follow-up for those patients alive without disease recurrence.

Embodiments may analyze clinical prognostic factors, including Eastern Cooperative Oncology Group (ECOG) performance status and TNM stage per the American Joint Committee on Cancer (AJCC) staging system. Clinical staging (e.g., overall stage IIIA vs. IIIB), tumor histology (e.g., adenocarcinoma or squamous cell carcinoma), procedure type (e.g., lobectomy or pneumonectomy), median radiation dose and nodal disease (N0, N1, N2), may be considered as clinical prognostic factors.

Embodiments may segment a tumor represented in the baseline CT image. Lung tumors may be contoured on 3D SLICER software. The peritumoral compartment around the nodule is defined via the use of quantitative morphological operations (e.g., dilation) as a region extending radially from the nodule boundary up to, in one embodiment, 15 mm. Embodiments may eliminate the effect of skin, air or lipids when the mask is extended. Automated segmentation techniques may be employed, including a region growing technique, thresholding, or a watershed approach, to segment the tumor and define the tumor boundary.

Embodiments extract radiomic features from the baseline CT image. Embodiments may determine which radiomic features are most discriminative of MPR post-TMT. In one embodiment, 1542 radiomic features from the intratumoral and peritumoral compartments were extracted from baseline CT scans. In this embodiment, 13 Haralick, 10 local binary pattern (LBP), and 20 histogram of oriented gradient (HOG) set of features are extracted. These radiomic features capture textural patterns and are predictive of variation in tumor microarchitecture, heterogeneity and local appearance of nodules. 13 co-occurrence of local anisotropy gradients (CoLIAGe) features, that capture textural entropy structural disorder by applying GLCM metrics of disorder to local dominant intensity gradients, were extracted. In addition to textural features, in this embodiment, 25 Law and 48 Gabor features are extracted from intra-tumoral and peritumoral regions. Law features are a filter-based descriptor that capture textural patterns while Gabor features capture different spatial frequencies within the image at directional orientations. Additionally, 24 computerized quantitative shape features were extracted, and evaluated in combination with texture features. The width, height, depth as well as sphericity features were calculated in 3D space. The remaining features were computed in 2D on a slice-by-slice basis. First-order statistics (mean, median, SD, skewness, and kurtosis) of each feature are computed across pixels and over slices containing the tumor.

Embodiments may determine which radiomic features are most discriminative of MPR. In one embodiment, feature selection was employed to rank and choose the most stable and predictive features. Highly stable (i.e., reproducible) features are selected based on evaluation of the test-retest RIDER lung CT dataset. The intra-class correlation coefficient (ICC) is calculated to quantify the consistency of the radiomic measurements between two scans performed on a patient. Features with a high ICC suggest that the radiomic features should be resilient to variations in CT scan time, institutions, sites, vendors and acquisition parameters (e.g. reconstruction slice thickness, contrast enhancement and convolutional kernel). In this embodiment, features with an ICC≥0.85 are considered as highly stable and reproducible. In this embodiment, minimum redundancy maximum relevance (mRMR) feature selection, which is an entropy-based feature selection approach, is employed to identify the most discriminating features from amongst those with an ICC>0.85. Other feature selection approaches may be employed.

Embodiments may perform logistic regression along with receiver operating characteristic (ROC) analysis to identify the radiomic features that are most predictive of MPR. Exact binomial 95% confidence intervals (CIs) are calculated for response rate to induction chemoradiotherapy and the rate of complete resection following induction therapy. Time-to-event data (e.g., OS, DFS) are analyzed using the Kaplan-Meier method with a log-rank test and Cox proportional hazard model to identify the important imaging features and clinical-pathologic covariates of OS and DFS.

Embodiments may employ a univariate analysis of OS and DFS using a log-rank test (for categorical variables) and Cox model (for continuous measurements) of radiomic features and clinico-pathologic variables. For binary outcome classification (e.g., MPR and non-MPR), variables with p<0.05 are introduced into a multivariable logistic regression model. To build the multivariate radiomic signature for time-to-event data (e.g., OS, DFS), embodiments may employ Cox regression models on the training set for selected prognostic variables. In one embodiment, all possible combinations of top texture features selected by mRMR are calculated and added to the model separately for predicting OS and DFS. Intermediate models are tested by repeated random sub-sampling based cross validation with one-hundred (100) iterations on the training set. The combination that results in the highest CI for each model is selected as the final model and used to construct a risk score for predicting OS and DFS. The risk score is calculated using a linear combination of those features with corresponding coefficients calculated by a multivariate Cox model.

Embodiments may analyze the training set for selecting top features for MPR. Within the training set, the regression classifier is iteratively trained with variables where p<0.05 and applied across one-hundred (100) iterations of three-fold cross-validation to first assess response prediction. The selected model is then validated on the test set for discriminating MPR from non-MPR.

In one embodiment, among the 1542 extracted features, a total of 1039 (67%) were identified as being highly stable, based off the intra-class correlation coefficient, ICC>0.85 threshold. From among these 1039 features, a further 13 features were selected using the mRMR feature selection method as being predictive of MPR. The average and variance ICC for these 13 selected features was 0.93±0.026, which indicates a high degree of reproducibility for the same day test-retest cases within the RIDER dataset.

Figure 4:
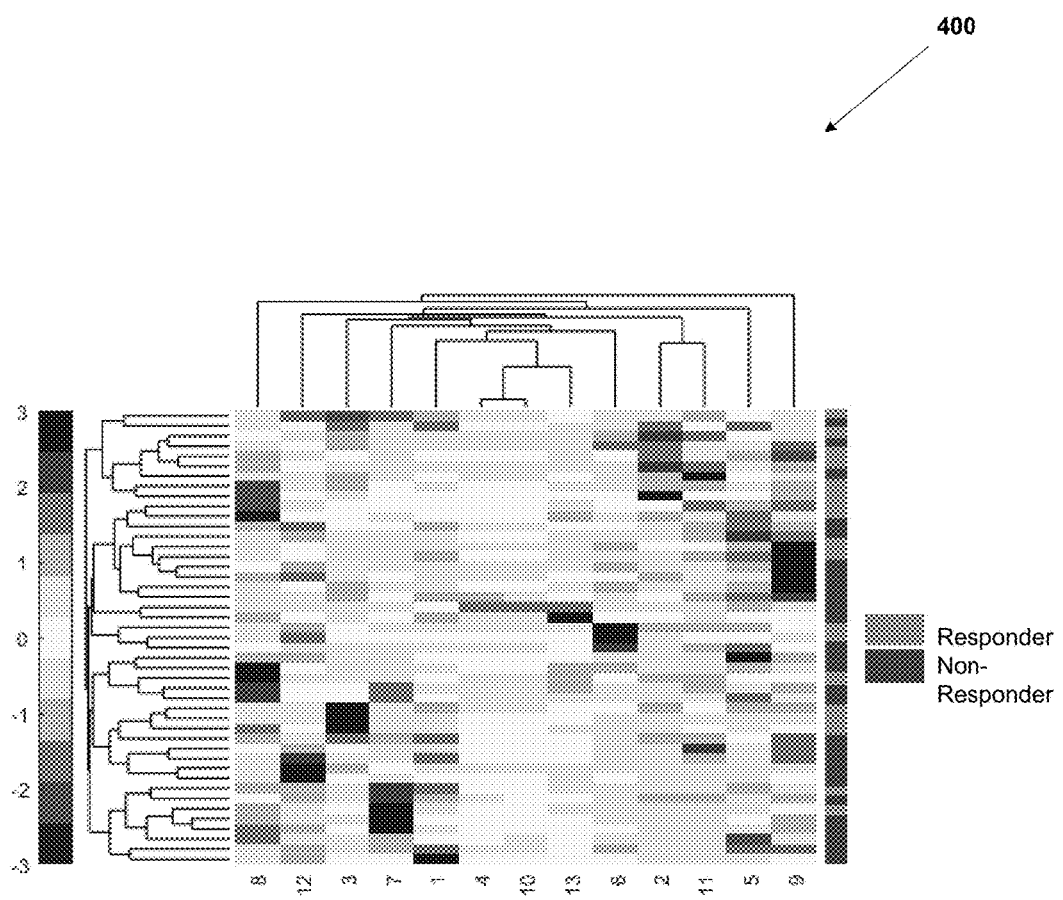
FIG. 4 illustrates an unsupervised hierarchical clustering feature expression heat map of discriminating features for predicting MPR.
Figure 6:
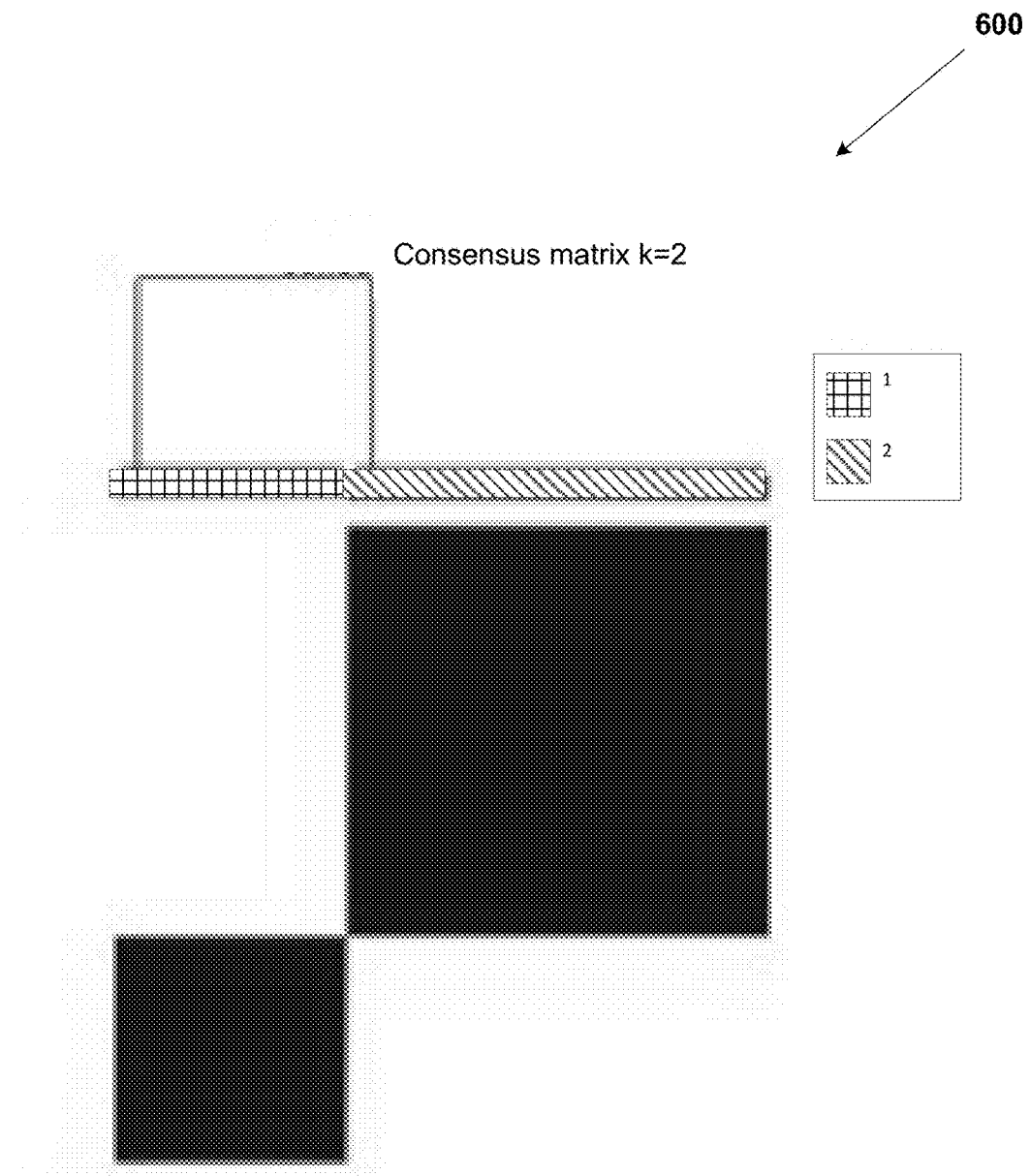
FIG. 6 illustrates consensus clustering using combined intratumoral and peritumoral radiomic features.

Embodiments may employ unsupervised clustering to identify differences in baseline CT imagery between patients who experience MPR post-TMT and patients who do not experience MPR post-TMT without any knowledge about output (rather than prediction). FIG. 4 illustrates an unsupervised hierarchal clustering feature expression heat map 400 of the most discriminating features for post-TMT responders and non-responders in a training set. The X-axis shows the feature expression while the Y-axis shows the different patients in the training set. The numbers on the X-axis correspond to each feature in table 500 illustrated in FIG. 5, respectively. A consensus clustering approach may also be employed to evaluate the discriminative ability of the combination of intratumoral and peritumoral features. FIG. 6 shows distinct response associated clusters obtained via a combination of intratumoral and peritumoral features according to embodiments described herein. FIG. 6 illustrates, a consensus matrix 600 where k=2, illustrating consensus clustering using combined intratumoral and peritumoral texture features. The two clusters have a preponderance of non-responders (56%) and responders (89%) respectively.

In one embodiment, multiple regression analysis of extracted radiomic features and clinico-pathologic variables is performed to evaluate discrimination of responders and non-responders in the training set. Features with p-value <0.05 are used to train a logistic regression classifier with the training set. In this embodiment, signature consists of four radiomic features, including a peritumoral Laws feature, an area of lesion feature, a peritumoral Law Laplacian feature, and an intratumoral Gabor feature, and two clinico-pathologic biomarkers, including lymphatic invasion (LVI) status and percentage of viable tumor. In this embodiment, the combined model yields an AUC of at least 0.92±0.045 on the training set and corresponding AUC of at least 0.88 for the independent test set, in discriminating MPR from non-MPR post-TMT.

Figure 7:
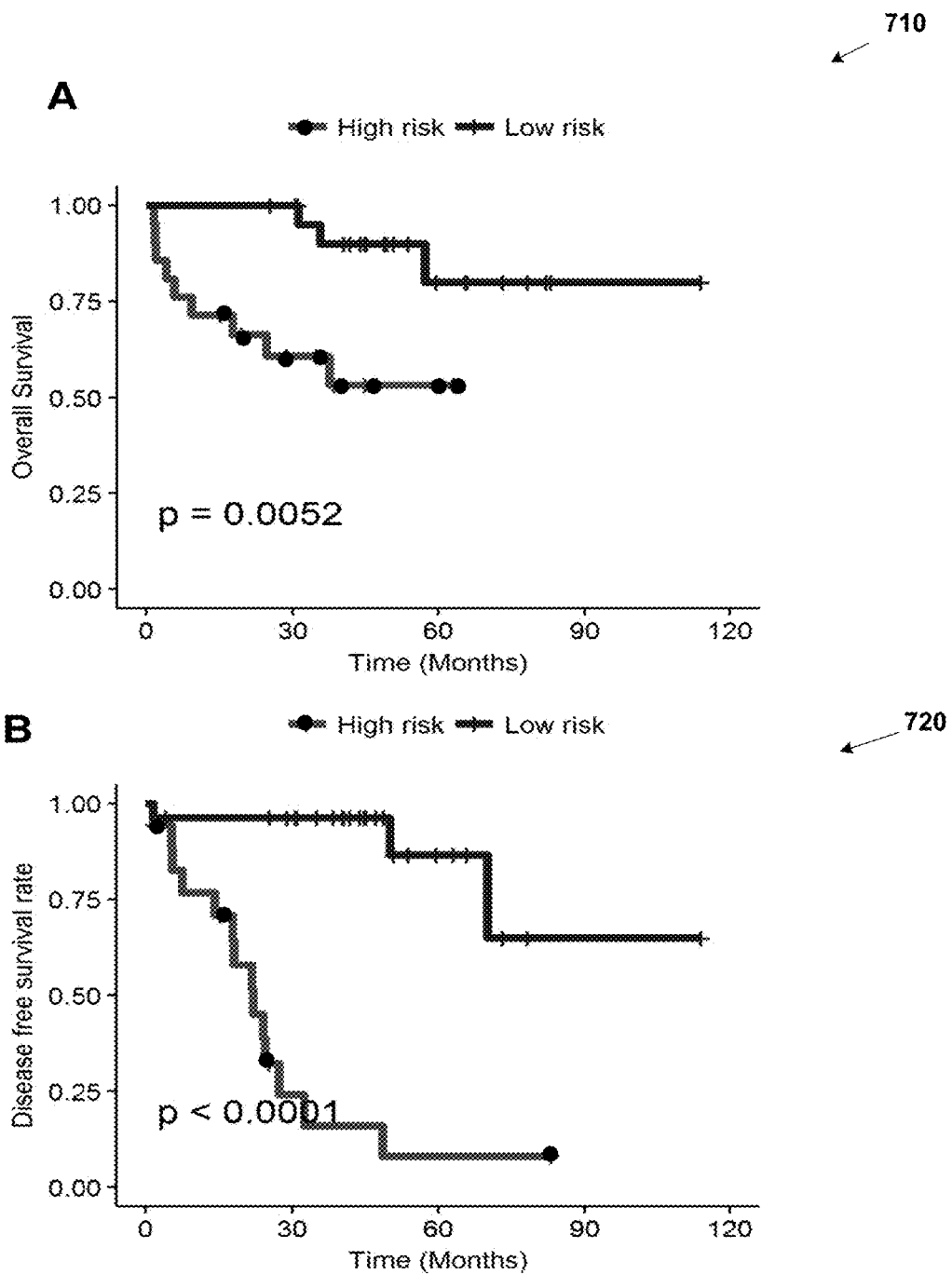
FIG. 7 illustrates Kaplan-Meier curves for a model predicting score to OS probability, and score to DFS rate.

Embodiments may also predict OS in NSCLC patients. Embodiments may extract radiomic features and select the most discriminating radiomic or clinical features for predicting OS. In one embodiment, embodiments may define a combination of radiomic and clinical features that yielded the maximum CI on the discovery set as the optimal signature (risk-score) for predicting OS (CI=0.85, Wald p-value=0.004). In this embodiment, the signature includes four radiomic texture features, including a peritumoral Law_Laplacian S5×R5 feature, a peritumoral Laws W5×S5 feature, a peritumoral Law_Laplacian W5×S5 feature, and an intratumoral Law_Laplacian W5×E5 feature, and one clinicopathologic biomarker. In this embodiment, the clinicopathologic biomarker is a percentage of viable tumor feature. A Cox regression analysis identifies the risk-score as an independent risk factor for OS, with HR: 3.18, 95% CI: 1.57-6.42, and p-value=0.0012. FIG. 7 includes graph 710, which illustrates a Kaplan Meier curve as described herein with the signature for predicting OS on the test set, indicating a significant difference between patients with low and high risk-scores (log-rank test, p-value=0.0052). In graph 710, the X axis indicates the time in months post TMT, while the Y axis indicates the overall survival probability.

Figure 8:
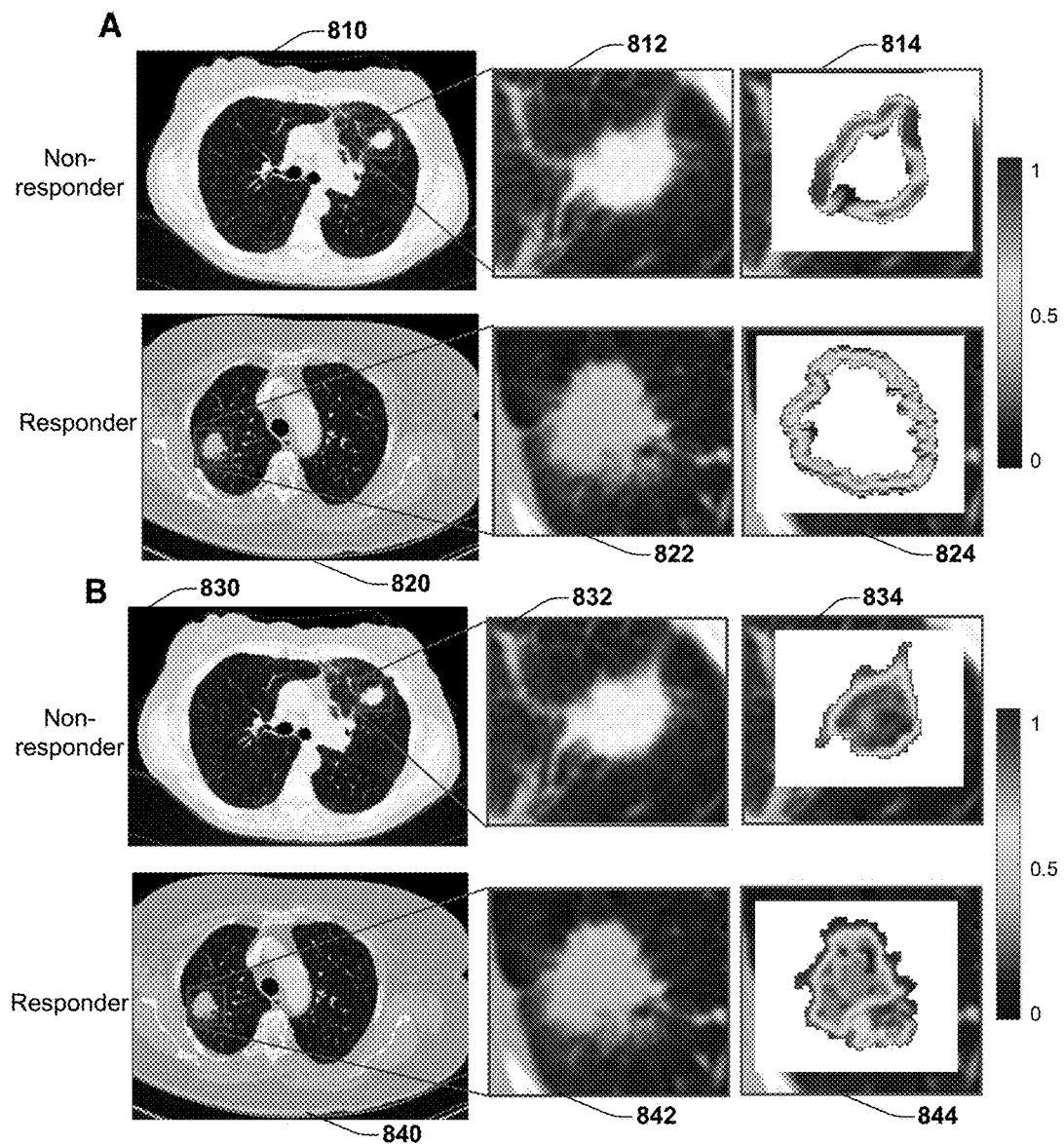
FIG. 8 illustrates radiomic feature maps for MPR and non-MPR lesions on baseline CT imagery.

Embodiments may also predict DFS in NSCLC patients. Embodiments may extract radiomic features from the baseline CT imagery and select the most discriminating radiomic or clinical features for predicting DFS. The most discriminating radiomic and clinical features for predicting DFS may be combined into a radiomic risk score signature. In one embodiment, a radiomic risk-score signature for predicting DFS includes five radiomic texture features, including a peritumoral Law_Laplacian S5×R5 feature, an intratumoral Laws E5×W5 feature, a peritumoral Law_Laplacian W5×S5 feature, an intratumoral Law_Laplacian E5×W5 feature, and an intratumoral Law_Laplacian W5×E5, and three clinicopathologic measurements, including a histology feature, an LVI feature, and a percentage of viable tumor feature. Patients with lower LVI and lower percentage of viable tumor may have better DFS than those with higher values. Embodiments, using a Cox regression analysis, identify that risk-score is an independent risk factor for DFS, with an HR: 2.72, 95% CI: 1.73-4.27, and a p-value of 1.4e-05. A median split of the risk-score signature on the test set yields a significant difference (log-rank test, p-value=7.3e-08) for DFS rate between low risk and high risk patients. FIG. 7 includes graph 720 which illustrates Kaplan Meier curves corresponding to DFS rate. The X axis in graph 720 indicates the time in months post TMT, while the Y axis indicates the disease free survival rate. The distribution statistics of the Laws and Law-Laplacian features, as captured by skewness and kurtosis, may be different between lesions that did and did not have MPR. FIG. 8 illustrates baseline CT imagery of MPR responders 820 and 840, and of MPR non-responders 810 and 830. Magnified tumoral regions are indicated at 812, 822, 832, and 842. Radiomic texture features of peritumoral regions are illustrated at 814 and 824. Radiomic texture features of tumoral regions are illustrated at 834 and 844. FIG. 8 illustrates how the presence of a higher textural pattern disorder or heterogeneity within and around non-MPR lesions compared to MPR lesions, expressed by a heatmap of the radiomic feature, on the baseline CT imagery is associated with MPR.

Embodiments that predict MPR post-TMT using tumoral and peritumoral radiomic features, as well as with clinicopathologic features, provide improved performance with respect to disease recurrence prognostic accuracy, compared to existing approaches and existing clinical variables. Embodiments thus improve the performance, including at least the accuracy of circuits, systems, apparatus, and computers that predict MPR post-TMT according to embodiments described herein, or that provide a recommendation to a medical practitioner regarding the suitability of a patient for TMT.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 is a flow diagram of example operations 100 that may be performed by a processor for predicting disease recurrence following TMT in NSCLC, including stage IIIA NSCLC. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 includes, at 110, accessing a baseline computed tomography (CT) image of a region of tissue (ROT) demonstrating NSCLC. The baseline CT image has a plurality of pixels, a pixel having an intensity. Accessing the baseline CT image includes acquiring electronic data, reading from a computer file, receiving a computer file, reading from a computer memory, or other computerized activity. In one embodiment, the baseline CT image is a non-contrast, pre-neoadjuvant chemotherapy CT image of a region of tissue demonstrating stage III NSCLC.

In one embodiment, the baseline CT image is acquired according to a set of imaging parameters. For example, the slice thickness may vary from 0.6 mm to 5 mm. The CT image may be acquired from multiple reconstruction kernels. The pixel sizes may range from 0.44×0.44 mm to 0.99×0.99 mm, and may have an average size of 0.75×0.75 mm. A slice may have a XY planar resolution of 512×512 pixels with a 16-bit gray scale resolution in Hounsfield Units (HU). Images may be reconstructed by standard (low pass) convolution kernels (e.g., Siemens: 'B321f', 'B35f'; Philips: 'B', 'C', 'D'; Toshiba: 'FC01', 'FC08', 'FC18'; GE: 'SOFT', 'STANDARD') or may be available for sharp (high pass) convolution kernels (e.g., Siemens: 'B321s', 'B35fs'; GE: 'LUNG'). In another embodiment, other imaging parameters may be employed.

The set of operations 100 also includes, at 120, segmenting a tumoral region represented in the baseline CT image. Segmenting the tumor region includes defining a tumoral boundary. Automated segmentation techniques may be employed, including a region growing technique, thresholding, or a watershed approach, to segment the tumor or define the tumor boundary.

The set of operations 100 also includes, at 130, defining a peritumoral region by performing a morphological operation on the tumoral boundary. Embodiments may define a peritumoral region using quantitative morphological operations on the tumoral boundary. For example, a peritumoral region may be defined as a region extending radially from the tumoral boundary. In one embodiment, the peritumoral region is defined by dilating the tumoral boundary radially 15 mm. In other embodiments, the peritumoral region may be defined by dilating the tumor boundary other distances (e.g., 10 mm, 12 mm). In other embodiments, other morphological operations may be employed to define the peritumoral region.

The set of operations 100 also includes, at 140, extracting a set of tumoral radiomic features from the tumoral region. In one embodiment, the set of tumoral radiomic features includes a Laplacian Law feature. In another embodiment, the set of tumoral features includes an area of lesion feature and a Gabor feature. Extracting the set of tumoral radiomic features includes acquiring electronic data, reading from a computer file, receiving a computer file, reading from a computer memory, or other computerized activity.

A Laws Laplacian feature includes Laplacian pyramids that allow for the capture of multi-scale edge representations via a set of bandpass filters. In one embodiment, the original image is convolved with a Gaussian kernel. The Laplacian is then computed as the difference between the original image and the low-pass-filtered image. The resulting image is then sub-sampled by a factor of 2, and the filter subsample operation is repeated recursively. This process is continued to obtain a set of bandpass-filtered images. Laws Energy filters are then applied to the resulting images to obtain a set of 25 features.

A Laws feature may include a Laws Energy measure. A Laws Energy measure includes a response to 5-pixel×5-pixel filter targeting a combination of specific textural enhancement patterns in the X and Y directions. Descriptors include combinations of five 1D filters: level (L), edge (E), spot (S), wave (W), and ripple (R). Laws energy measures remove effects of illumination by moving a small window around the image and subtracting the local average from each pixel.

The set of operations 100 also includes, at 150, extracting a set of peritumoral radiomic features from the peritumoral region. In one embodiment, the set of peritumoral radiomic features includes a Laws Laplacian feature. In another embodiment, the set of peritumoral radiomic features includes a Laws feature and a Laws Laplacian feature. Extracting the set of peritumoral radiomic features includes acquiring electronic data, reading from a computer file, receiving a computer file, reading from a computer memory, or other computerized activity.

The set of operations 100 also includes, at 160, extracting a set of clinico-pathologic features from the baseline CT image. In one embodiment, the set of clinico-pathologic features includes an LVI status feature. In another embodiment, the set of clinico-pathologic features includes an LVI feature and a percent viable tumor feature. Extracting the set of clinico-pathologic features includes acquiring electronic data, reading from a computer file, receiving a computer file, reading from a computer memory, or other computerized activity.

The set of operations 100 also includes, at 170, providing the set of tumoral radiomic features, the set of peritumoral radiomic features, and the set of clinico-pathologic features to a machine learning classifier. Providing the set of tumoral radiomic features, the set of peritumoral radiomic features, and the set of clinico-pathologic features to the machine learning classifier includes acquiring electronic data, reading from a computer file, receiving a computer file, reading from a computer memory, or other computerized activity. In one embodiment, the machine learning classifier is a multivariable logistic regression (MLR) classifier. The machine learning classifier may be trained using three-fold cross-validation of radiomic features extracted from baseline CT images on a training set. A member of the training set includes at least one baseline CT image of a region of tissue that experienced MPR post TMT, and at least one different baseline CT image of a region of tissue that did not experience MPR post TMT. The machine learning classifier may be validated using a validation set of baseline CT images that includes at least one baseline CT image of a region of tissue that experienced MPR post TMT, and at least one different baseline CT image of a region of tissue that did not experience MPR post TMT. In another embodiment, the machine learning classifier may be another type of machine learning classifier or deep learning classifier, including a support vector machine (SVM) classifier, a quadratic discriminant analysis (QDA) classifier, a linear discriminant analysis (LDA) classifier, a random forests classifier, or a convolutional neural network.

The set of operations 100 also includes, at 180, receiving, from the machine learning classifier, a time-to-recurrence post-trimodality therapy (TMT) prediction. The time-to-recurrence post-TMT prediction provides a discrimination between low risk and high risk of recurrence post-TMT prediction for the region of tissue represented in the baseline CT image. The discrimination between high and low risk to recurrence post-TMT prediction is based on the set of tumoral radiomic features, the set of peritumoral radiomic features, and the set of clinico-pathologic features (e.g., on the risk-score signature). Receiving the prediction includes acquiring electronic data, reading from a computer file, receiving a computer file, reading from a computer memory, or other computerized activity.

The set of operations 100 also includes, at 190, generating a classification of the ROT as an MPR responder or MPR non-responder by classifying the ROT as an MPR responder or MPR non-responder. Embodiments may generate the classification based, at least in part, on the discrimination between low and high risk to recurrence post-TMT prediction. Embodiments classify the ROT as an MPR responder or MPR non-responder with an area under the curve of at least 0.92.

The set of operations 100 also includes, at 192, displaying the classification. Displaying the classification may include displaying the classification on a computer monitor, a smartphone display, a tablet display, or other displays. Displaying the classification may also include printing the classification. Displaying the classification may also include controlling a computer assisted diagnosis (CADx) system, a monitor, or other display, to display operating parameters or characteristics of a machine learning classifier, including the first machine learning classifier or the second, different machine learning classifier, during both training and testing, or during clinical operation of the machine learning classifier. By displaying the classification, example embodiments provide a timely and intuitive way for a human pathologist to more accurately classify pathologies demonstrated by a patient, thus improving on existing approaches to selecting patients for TMT, or to generate a personalized NSCLC treatment plan.

Figure 2:
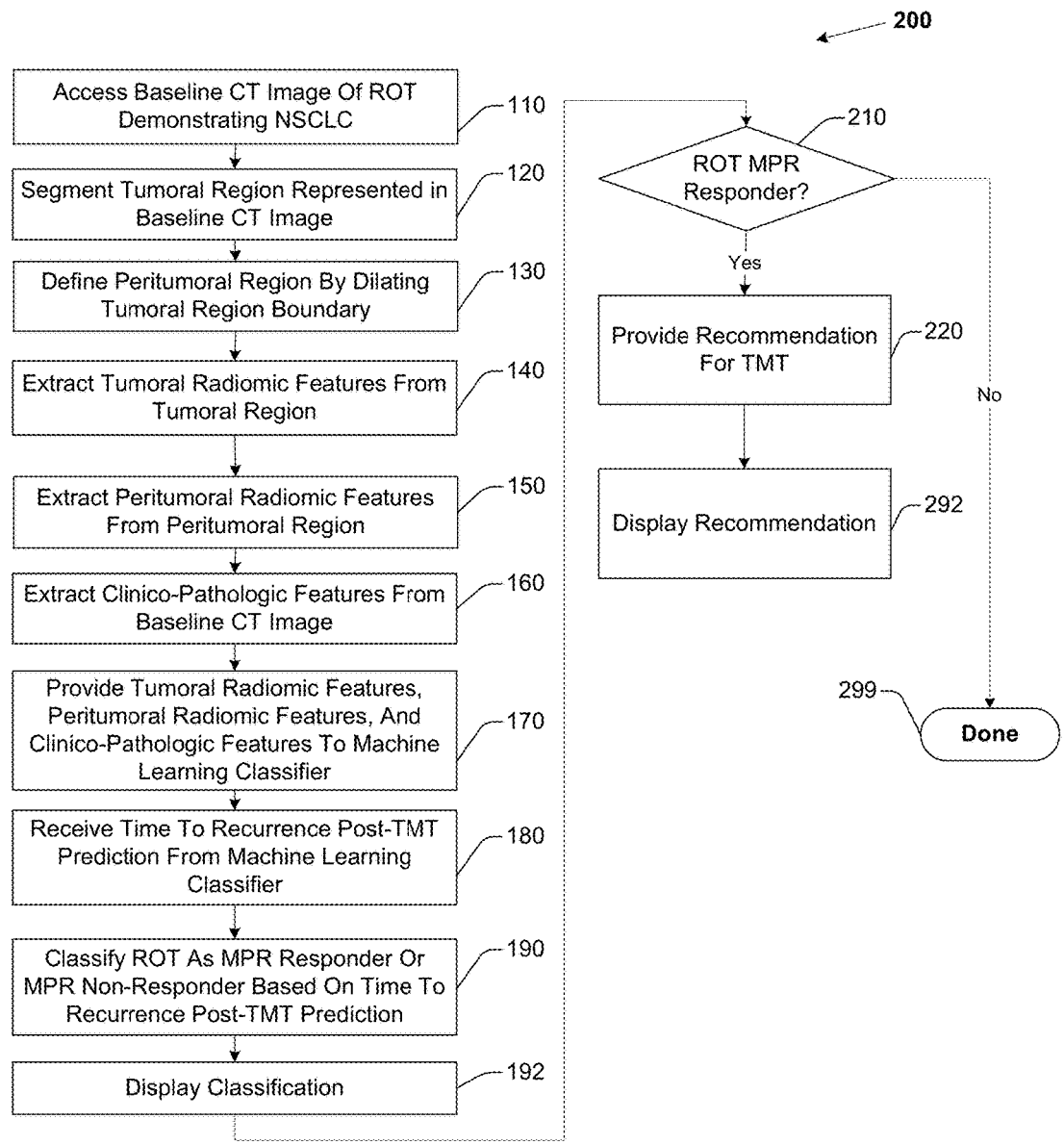
FIG. 2 is a flow diagram of example operations for predicting MPR in NSCLC.

FIG. 2 illustrates a set of operations 200 that is similar to operations 100 but that includes additional elements and details. The set of operations 200 includes, at 210, determining if the classification is "MPR responder". The set of operations also includes, upon determining that the classification is MPR responder, at 220, providing a recommendation of the ROT for TMT. For example, embodiments may provide a recommendation that the patient from which the imagery of the ROT was acquired receive TMT. The set of operations 200 further includes, at 292, displaying the recommendation. If it is determined at 210 that the classification is not MPR responder (e.g., MPR non-responder), the set of operations 200 may provide a recommendation to not provide TMT, terminate at 299, return control to another process, or perform other actions. In one embodiment, determining that the classification is MPR responder may include determining if the time-to-recurrence post TMT prediction is above a threshold level.

Embodiments may predict OS in NSCLC patients. In one embodiment, a set of tumoral radiomic features, a set of peritumoral radiomic feature, and a set of clinico-pathologic features are extracted from the baseline CT image. In this embodiment, the set of tumoral radiomic features, the set of peritumoral radiomic feature, and the set of clinico-pathologic features includes a linear combination of four radiomic texture features, including a peritumoral Law_Laplacian S5×R5 feature, a peritumoral Laws W5×S5 feature, a peritumoral Law_Laplacian W5×S5 feature, and an intratumoral Law_Laplacian W5×E5 feature, and one clinico-pathologic biomarker, including a percentage of viable tumor feature. In one embodiment, the machine learning classifier generates an OS prediction based, at least in part, on the set of tumoral radiomic features, the set of peritumoral radiomic features, and the set of clinico-pathologic features. In one embodiment, a median split of the risk-score signature is computed based, at least in part, on the set of tumoral radiomic features, the set of peritumoral radiomic features, and the set of clinico-pathologic features, and used to predict OS for high risk and low risk patients. In one embodiment, the operations further comprising displaying the OS prediction. Embodiments may generate a recommendation for TMT based, at least in part, on the OS prediction.

Embodiments may predict DFS in NSCLC patients. In one embodiment, the set of tumoral radiomic features includes a Law_Laplacian W5 by E5 feature. In this embodiment, the set of peritumoral radiomic features includes a Law_Laplacian W5 by S5 feature. In this embodiment, the set of clinico-pathologic features includes a histology feature, an LVI status feature, and a percentage of viable tumor feature. In one embodiment, the tumoral radiomic features, the peritumoral radiomic features, and the clinico-pathologic features are provided to a machine learning classifier which computes a DFS prediction based on the provided features. In one embodiment, the features are used to generate a risk-score. In this embodiment, the median split of the risk-score signature is used to predict DFS rate in patients with a high risk or low risk of recurrence. The prediction is based, at least in part, on the set of tumoral radiomic features, the set of peritumoral radiomic features, and the set of clinico-pathologic features. In this embodiment, the set of operations may further include displaying the DFS prediction. Embodiments may generate a TMT recommendation based, at least in part, on the DFS prediction.

In another embodiment, the set of tumoral radiomic features or the set of peritumoral radiomic features may include other, different radiomic features. For example, embodiments may extract a Gabor feature, a Haralick feature, a Local Binary Pattern (LBP) feature, a Histogram of Oriented Gradient (HOG) feature, a Co-occurrence of Local Anisotropic Gradient Orientations (CoLlAGe) feature, or a three dimensional (3D) shape feature.

Gabor features include detection of edges through response to Gabor wavelet features. Each descriptor quantifies response to a given Gabor filter at a specific frequency (f∈{0, 2, 4, 8, 16, or 32}) and orientation (θ∈{0, π/8, π/4, 3π/8, π/2, 5π/8, 3π/4, 7π/8}). Gabor features segregate images having regions differing in one of the following properties: density of elements, orientation, phase and energy.

Haralick features quantify heterogeneity and entropy of local intensity texture as represented by a gray-level co-occurrence matrix within a 5-pixel by 5-pixel window.

LBP features summarize the local structure in an image by comparing each pixel with its neighborhood and generating a binary vector related to the intensity of the center pixels. The LBP process results in an 8-bit code-word describing a local neighborhood around a pixel.

HOG features reflect the frequency of occurrences of intensity gradient orientation in localized image regions. The image is divided into small connected cells and for each cell, the number of occurrences of each gradient direction calculated. The combination of these histograms yields the corresponding HOG features.

CoLlAGe features involve extracting the dominant gradient orientation along the X and Y directions for every pixel, or subset of pixels, in an image via principal component analysis. A co-occurrence matrix is then computed for every pixel, or subset of pixels, within the neighborhood (5 pixels by 5 pixels) to capture co-occurring arrangements of the dominant gradient orientations. CoLlAGe features detect local differences in voxel-level gradient orientations for distinguishing similar appearing phenotypes at a level that the human eye is unable to detect.

3D shape features may include measures of convexity, width, height, depth, perimeter, area, eccentricity, compactness, radial distance, roughness, elongation equivalent diameter or 3D-sphericity of the nodule (i.e., tumor).

Embodiments may further include generating a personalized NSCLC treatment plan. The personalized NSCLC treatment plan is based, at least in part, on the classification. The personalized NSCLC treatment plan may be further based on the OS prediction, or the DFS prediction. Generating a personalized treatment plan facilitates the technical effect of delivering a particular treatment that will be therapeutically active to the patient, while minimizing negative or adverse effects experienced by the patient. For example, the personalized treatment plan may suggest TMT, may suggest a particular surgical treatment, may define an immunotherapy agent dosage or schedule, or a chemotherapy agent dosage or schedule, when the region of tissue is classified as a post-TMT MPR responder. For a region of tissue where post-TMT MPR is unlikely, other treatments may be suggested. Similarly, the personalized treatment plan may suggest a first treatment (e.g., TMT) for an MPR responder, and suggest a second, different treatment for a non-responder.

In one embodiment, the operations may further include training a machine learning classifier. In this embodiment, the machine learning classifier is trained and tested using a training set of images and a testing set of images. The training set of images and the testing set of images include imagery from patients that experienced MPR, and patients that did not experience MPR. The training set and the testing set may be selected, in one embodiment, as illustrated in FIG. 3. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates the training. Other training termination conditions may be employed. Training the machine learning classifier may also include determining which radiomic features or which clinico-pathologic features, or combination of radiomic and clinico-pathologic features, are most discriminative in distinguishing tissue likely to experience MPR post-TMT from tissue unlikely to experience MPR post-TMT.

While FIGS. 1 and 2 illustrate various actions occurring in serial, it is to be appreciated that various actions illustrated in FIGS. 1 and 2 could occur substantially in parallel. By way of illustration, a first process could involve accessing a first baseline CT image, a second process could involve extracting radiomic features from the first baseline CT image, and a third process could involve accessing a second baseline CT image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 100 or 200, method 1100, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved selection of patients for TMT based on, for example, improved prediction of MPR post-TMT, prediction of OS, or prediction of DFS, may produce the technical effect of improving treatment efficacy by increasing the accuracy of and decreasing the time required to treat patients demonstrating NSCLC, or other forms of cancerous pathology. Treatments and resources, including expensive immunotherapy agents or chemotherapy may be more accurately tailored to patients with a higher likelihood of MPR post-TMT, so that more appropriate treatment protocols may be employed, and expensive resources are not wasted. Controlling a personalized medicine system, a CADx system, a processor, or an MPR post-TMT prediction system based on improved, more accurate prediction of MPR post-TMT or classification of tissue further improves the operation of the system, processor, or apparatus, at least because the accuracy of the system, processor, or apparatus is increased, and unnecessary operations will not be performed.

Embodiments described herein, including at least the sets of operations 100 and 200, apparatus 900 and 1000, method 1100, and computer 1200, resolve features extracted from baseline CT imagery at a higher order or higher level than a human can resolve in the human mind or with pencil and paper. For example, Laws Laplacian features are not properties of the tissue that a human eye can perceive. NSCLC tissue does not include a set of pixels with intensities, graphs, or entropy features, and these features cannot be stored in a human mind. Embodiments described herein use a combined order of specific rules, elements, operations, or components that render information into a specific format that is then used and applied to create desired technical results more accurately, more consistently, and with greater reliability than existing approaches, thereby producing the technical effect of improving the performance of the machine, computer, or system with which embodiments are implemented.

Using a more appropriately modulated treatment may lead to less aggressive therapeutics being required for a patient or may lead to avoiding or delaying a biopsy, a resection, or other invasive procedure. When patients demonstrating NSCLC who are likely to experience MPR post-TMT are more accurately distinguished from patients who are unlikely to experience MPR post-TMT, patients most at risk may receive a higher proportion of scarce resources (e.g., therapeutics, physician time and attention, hospital beds) while those less likely to benefit from the treatment, including TMT, or less in need, may be spared unnecessary treatment, which in turn spares unnecessary expenditures and resource consumption. Example operations, methods, apparatus, and other embodiments may thus have the additional technical effect of improving patient outcomes and reducing patient suffering compared to existing approaches.

Figure 9:
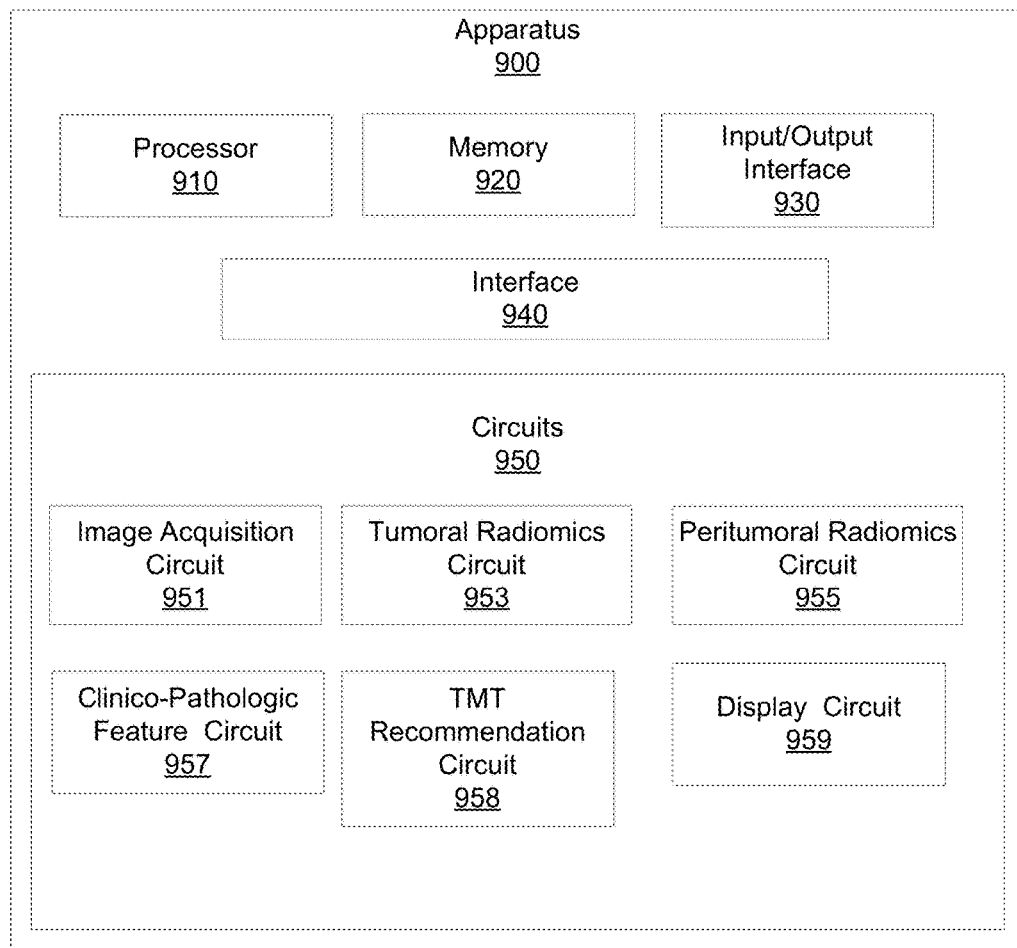
FIG. 9 illustrates an example apparatus for predicting MPR in NSCLC according to embodiments described herein.

FIG. 9 illustrates an example apparatus 900 for generating a recommendation that a patient receive TMT for NSCLC. Apparatus 900 includes a processor 910. Apparatus 900 also includes a memory 920. Processor 910 may, in one embodiment, include circuitry such as, but not limited to, one or more single-core or multi-core processors. Processor 910 may include any combination of general-purpose processors and dedicated processors (e.g., graphics processors, application processors, etc.). The processors may be coupled with or may include memory (e.g. memory 920) or storage and may be configured to execute instructions stored in the memory 920 or storage to enable various apparatus, applications, or operating systems to perform the operations. Memory 920 is configured to store a digitized baseline non-contrast CT image of a region of tissue demonstrating NSCLC. The image has a plurality of pixels, a pixel having an intensity. Memory 920 may be further configured to store a training set that includes a plurality of digitized CT images, where a member of the plurality of digitized CT images includes a region of tissue demonstrating NSCLC, and where a first subset of the training set includes images of tissue that experienced MPR post-TMT, and a second, different subset of the training set includes images of tissue that did not experience MPR post-TMT. Memory 920 may be further configured to store a testing set that includes a plurality of digitized CT images, where a member of the plurality of digitized CT images includes a region of tissue demonstrating NSCLC, and where a first subset of the testing set includes images of tissue that experienced MPR post-TMT, and a second, different subset of the testing set includes images of tissue that did not experience MPR post-TMT.

Apparatus 900 also includes an input/output (I/O) interface 930, a set of circuits 950, and an interface 940 that connects the processor 910, the memory 920, the I/O interface 930, and the set of circuits 950. I/O interface 930 may be configured to transfer data between memory 920, processor 910, circuits 950, and external devices, for example, a CADx system or a personalized medicine system.

The set of circuits 950 includes an image acquisition circuit 951, a tumoral radiomics circuit 953, a peritumoral radiomics circuit 955, a clinico-pathologic feature circuit 957, a TMT recommendation circuit 958, and a display circuit 959.

Image acquisition circuit 951 is configured to access a digitized baseline non-contrast CT image of an ROT demonstrating NSCLC. The baseline CT image includes a tumoral region and a peritumoral region. The baseline CT image has a plurality of pixels, a pixel having an intensity. In one embodiment, accessing the baseline CT image may include accessing an electronic file stored in a data storage device, including a hard disk drive, a solid state device, a tape drive, accessing a digitized baseline CT image over a local area network, or from the cloud. Accessing a baseline CT image includes acquiring electronic data, reading from a computer file, receiving a computer file, reading from a computer memory, or other computerized activity.

Tumoral radiomics circuit 953 is configured to extract a set of tumoral radiomic features from the tumoral region. The set of tumoral radiomic features includes an area of lesion feature and a Gabor feature. Tumoral radiomics circuit 953 may be further configured to segment the tumoral region, including defining a tumoral boundary.

Peritumoral radiomics circuit 955 is configured to extract a set of peritumoral radiomic features from the peritumoral region. The set of peritumoral radiomic features includes a Laws feature and a Law_Laplacian feature. Peritumoral radiomics circuit 955 may be further configured to define the peritumoral region by performing a morphological operation (e.g., dilation) on the tumoral boundary.

Clinico-pathologic feature circuit 957 is configured to extract a set of clinico-pathologic features from the ROT. In one embodiment, the set of clinico-pathologic features includes an LVI feature and a percent viable tumor feature. In another embodiment, the set of clinico-pathologic features may include other, different clinico-pathologic features.

TMT recommendation circuit 958 is configured to compute a probability that the ROT will experience post-TMT MPR based on the set of tumoral features, the set of peritumoral features, and the set of clinico-pathologic features. TMT recommendation circuit 958 is also configured to generate a recommendation for TMT based on the probability. For example, TMT recommendation circuit 958 may generate a recommendation that the patient of which the baseline CT image was acquired receive TMT upon determining that the probability that the ROT will experience post-TMT MPR is above a threshold probability.

Display circuit 959 is configured to display the recommendation. In one embodiment, display circuit 959 is also configured to display the probability that the ROT will experience post-TMT MPR, the set of tumoral radiomic features, the set of peritumoral radiomic features, the set of clinico-pathologic features, or the baseline CT image. Displaying the probability that the ROT will experience post-TMT MPR, the set of tumoral radiomic features, the set of peritumoral radiomic features, the set of clinico-pathologic features, or the baseline CT image may also include printing the probability that the ROT will experience post-TMT MPR, the set of tumoral radiomic features, the set of peritumoral radiomic features, the set of clinico-pathologic features, or the baseline CT image.

Display circuit 959 may also control a CADx system, a monitor, or other display, to display operating parameters or characteristics of the set of circuits 950, including, including a machine learning classifier, during both training and testing, or during clinical operation of apparatus 900 or apparatus 1000.

In one embodiment of apparatus 900 or apparatus 1000, the set of tumoral radiomic features includes a Law_Laplacian W5 by S5 feature, the set of peritumoral radiomic features includes a Laws W5 by S5 feature and a Law_Laplacian W5 by S5 feature, and the set of clinico-pathologic features includes a percent viable tumor feature. In this embodiment, TMT recommendation circuit 958 is further configured to generate an OS prediction based on the set of tumoral features, the set of peritumoral features, and the set of clinico-pathologic features. TMT recommendation circuit 958 is, in this embodiment, further configured to generate a recommendation for TMT based on the OS prediction. In this embodiment, display circuit 959 is further configured to display the OS prediction.

In one embodiment of apparatus 900 or apparatus 1000, the set of tumoral radiomic features includes a Law_Laplacian W5 by E5 feature, the set of peritumoral radiomic features includes a Law_Laplacian W5 by S5 feature, and the set of clinico-pathologic features includes a histology feature, an LVI status feature, and a percentage of viable tumor feature. In this embodiment, TMT recommendation circuit 958 is further configured to generate a DFS prediction based on the set of tumoral features, the set of peritumoral features, and the set of clinico-pathologic features. In this embodiment, TMT recommendation circuit is also further configured to generate a recommendation for TMT based on the DFS prediction. In this embodiment, display circuit 959 is further configured to display the DFS prediction.

Apparatus 1000 is similar to apparatus 1000, but includes additional elements and details. Apparatus 1000 includes personalized treatment plan circuit 1051. Personalized treatment plan circuit 1051 may be configured to generate a personalized treatment plan based, at least in part, on the recommendation for TMT. In one embodiment, the personalized treatment plan is further based on the probability that the ROT will experience post-TMT MPR, the OS prediction, the DFS prediction, the set of tumoral radiomic features, the set of peritumoral radiomic features, the set of clinico-pathologic features, or the baseline CT image. The personalized treatment plan may suggest a surgical treatment, may define an immunotherapy agent dosage or schedule, or a chemotherapy agent dosage or schedule, when the region of tissue has a higher likelihood of experience post-TMT MPR. For a region of tissue having a lower likelihood of post-TMT MPR, other treatments, schedules, or dosages may be suggested. In this embodiment, display circuit 959 may be configured to further display the personalized treatment plan.

In one embodiment, apparatus 900 or apparatus 1000 may also include a training circuit. The training circuit may be configured to train TMT recommendation circuit 958 according to techniques described herein. Training TMT recommendation circuit 958 may include training a machine learning classifier, including an SVM classifier or other type of machine learning or deep learning classifier. In one embodiment, the training circuit is configured to access a training dataset of digitized baseline CT images of a region of tissue demonstrating NSCLC. The training dataset includes digitized baseline CT images of tissue that experienced MPR post-TMT, and digitized baseline CT images of tissue that did not experience MPR post-TMT. The training dataset may include digitized baseline CT images of tissue that experienced MPR at different times, for example, images of tissue with short-term MPR, and images of tissue with long-term MPR. The training circuit may be further configured to access a testing dataset of digitized baseline CT images of a region of interest demonstrating NSCLC, where the testing dataset includes digitized baseline CT images of tissue that experienced MPR post-TMT, and digitized baseline CT images of tissue demonstrating NSCLC that did not experience MPR post-TMT. In this embodiment, the machine learning classifier is trained and tested using the training dataset of images and the testing dataset of images respectively.

Training the machine learning classifier may include training the machine learning classifier using a first set of tumoral radiomic features, a first set of peritumoral radiomic features, and a first set of clinico-pathologic features, or with a second, different set of tumoral radiomic features, a second, different set of peritumoral radiomic features, and a second, different set of clinico-pathologic features. For example, the first set of tumoral radiomic features, first set of peritumoral radiomic features, and first set of clinico-pathologic features may be used to train the machine learning classifier to distinguish MPR from non-MPR, while the second, different set of tumoral radiomic features, second, different set of peritumoral radiomic features, and second, different set of clinico-pathologic features may be used to train the machine learning classifier to predict high and low risk of OS or DFS. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

Figure 10:
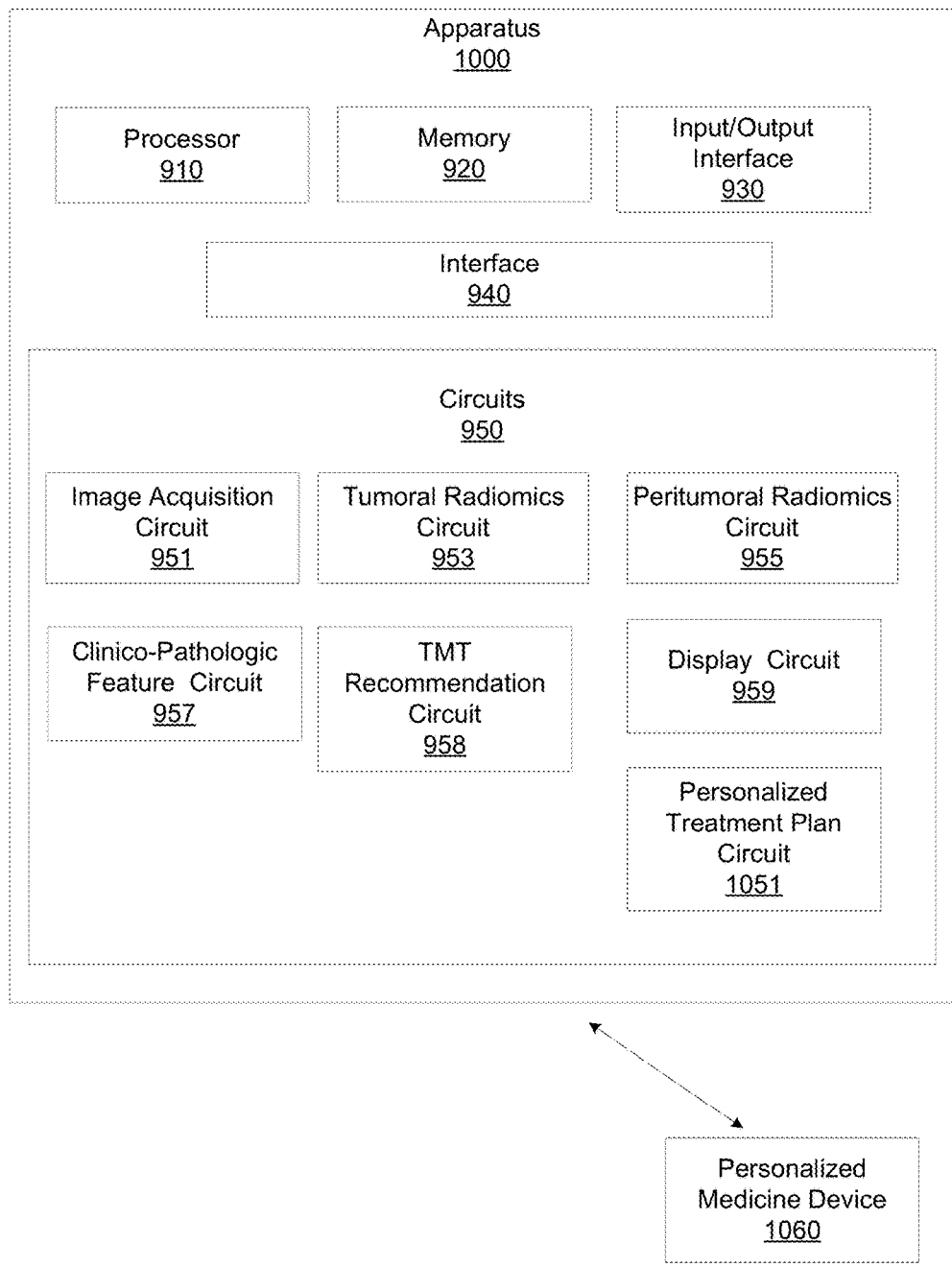
FIG. 10 illustrates an example apparatus for predicting MPR in NSCLC according to embodiments described herein.

FIG. 10 further illustrates a personalized medicine device 1060. Apparatus 1000 may be configured to transmit at least one of the TMT recommendation, the probability that the ROT will experience post-TMT MPR, the OS prediction, the DFS prediction, the baseline CT image, or the personalized treatment plan to the personalized medicine device 1060. Personalized medicine device 1060 may be, for example, a CADx system, a NSCLC post-TMT MPR prediction system, or other type of personalized medicine device that may be used to facilitate the classification of tissue or prediction of post-TMT MPR. In one embodiment, apparatus 1000 may control personalized medicine device 1060 to display at least one of the TMT recommendation, the probability that the ROT will experience post-TMT MPR, the OS prediction, the DFS prediction, the baseline CT image, or the personalized treatment plan on a computer monitor, a smartphone display, a tablet display, or other displays.

Figure 11:
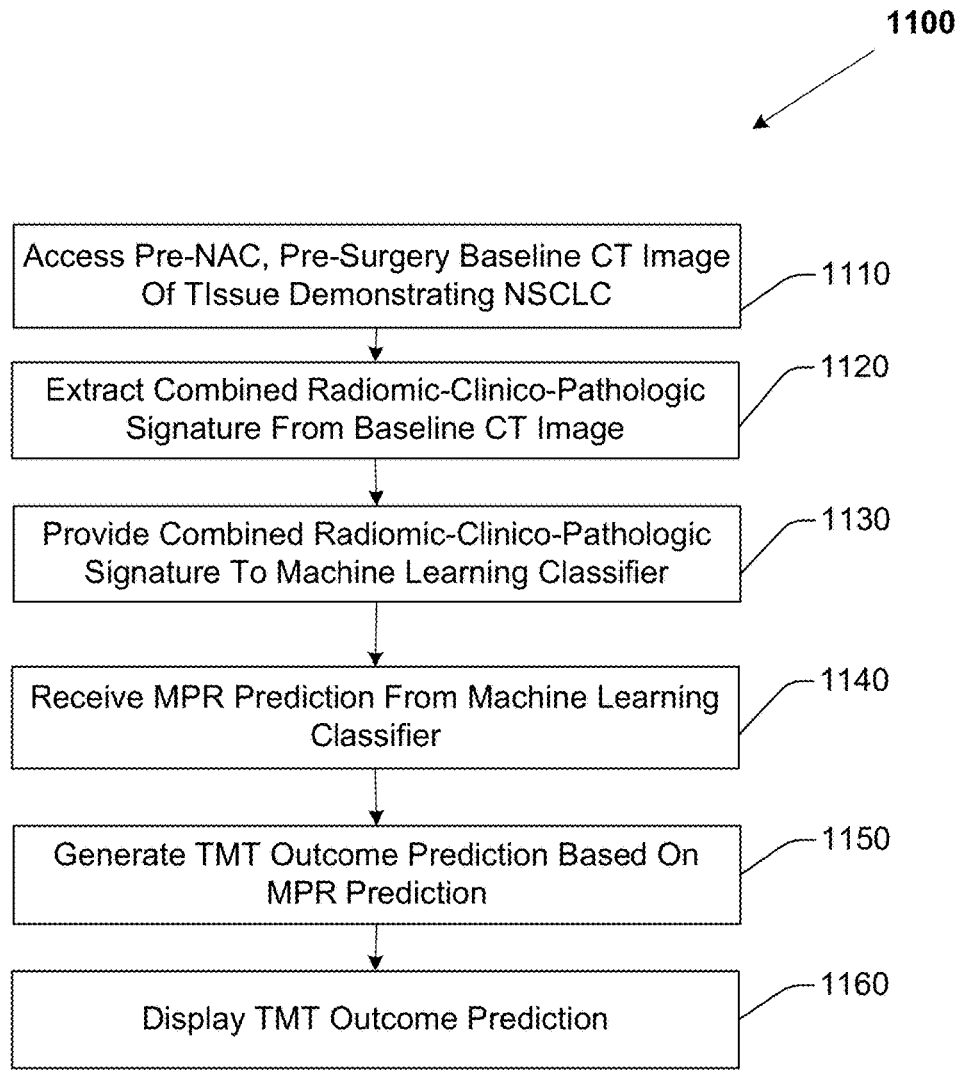
FIG. 11 illustrates an example method for predicting TMT outcome.

FIG. 11 illustrates an example method 1100 for predicting outcome of trimodality therapy in NSCLC. Method 1100 includes, at 1110 accessing a pre-neoadjuvant chemotherapy, pre-surgery, baseline CT image of a region of tissue demonstrating NSCLC. The region of tissue has a tumor region and a peritumoral region. The baseline CT image has a plurality of pixels, a pixel having an intensity. Accessing the baseline CT image includes acquiring electronic data, reading from a computer file, receiving a computer file, reading from a computer memory, or other computerized activity.

Method 1100 also includes, at 1120, extracting a combined radiomic risk signature from the baseline CT image. The combined radiomic-risk signature includes at least one radiomic feature extracted from the tumoral region, at least one radiomic feature extracted from the peritumoral region, and at least one clinico-pathologic feature.

Method 1100 also includes, at 1130, providing the combined radiomic-pathomic signature to a machine learning classifier. The machine learning classifier computes a MPR prediction based on the combined radiomic risk signature. In one embodiment, the machine learning classifier may generate a DFS prediction, or an OS prediction. In one embodiment, computing the DFS prediction may include computing a high risk or low risk of DFS rate prediction based on the combined radiomic risk signature. In one embodiment, computing the OS prediction may include computing a high risk or low risk of OS prediction based on the combined radiomic risk signature.

Method 1100 also includes, at 1140, receiving, from the machine learning classifier, the MPR prediction. Method 1100 may also include at 1140 receiving, from the machine learning classifier, the high risk or low risk of DFS rate prediction, or the OS prediction. Receiving the MPR prediction, the DFS prediction, or the OS prediction includes acquiring electronic data, reading from a computer file, receiving a computer file, reading from a computer memory, or other computerized activity. In another embodiment, method 1100 includes, at 1140, computing a risk score that is predictive of a high risk or low risk of DFS, generating a DFS prediction based on the risk score, or generating an overall survival (OS) prediction based on the combined radiomic risk signature.

Method 1100 also includes, at 1150, generating a TMT outcome prediction based on the MPR prediction, the DFS prediction, or the OS prediction. Generating the TMT outcome prediction includes acquiring electronic data, reading from a computer file, receiving a computer file, reading from a computer memory, or other computerized activity.

Method 1100 also includes, at 1160, displaying the TMT outcome prediction and at least one of the MPR prediction, the DFS prediction, or the OS prediction. Displaying the TMT outcome prediction and at least one of the MPR prediction, the DFS prediction, or the OS prediction may include controlling a computer monitor, a smartphone display, a tablet display, or other electronic display to display the TMT outcome prediction and at least one of the MPR prediction, the DFS prediction, or the OS prediction. Method 1100 may further include generating a recommendation that the patient of which the baseline CT image was acquired receive TMT, or not receive TMT, based, at least in part, on the TMT outcome prediction.

Figure 12:
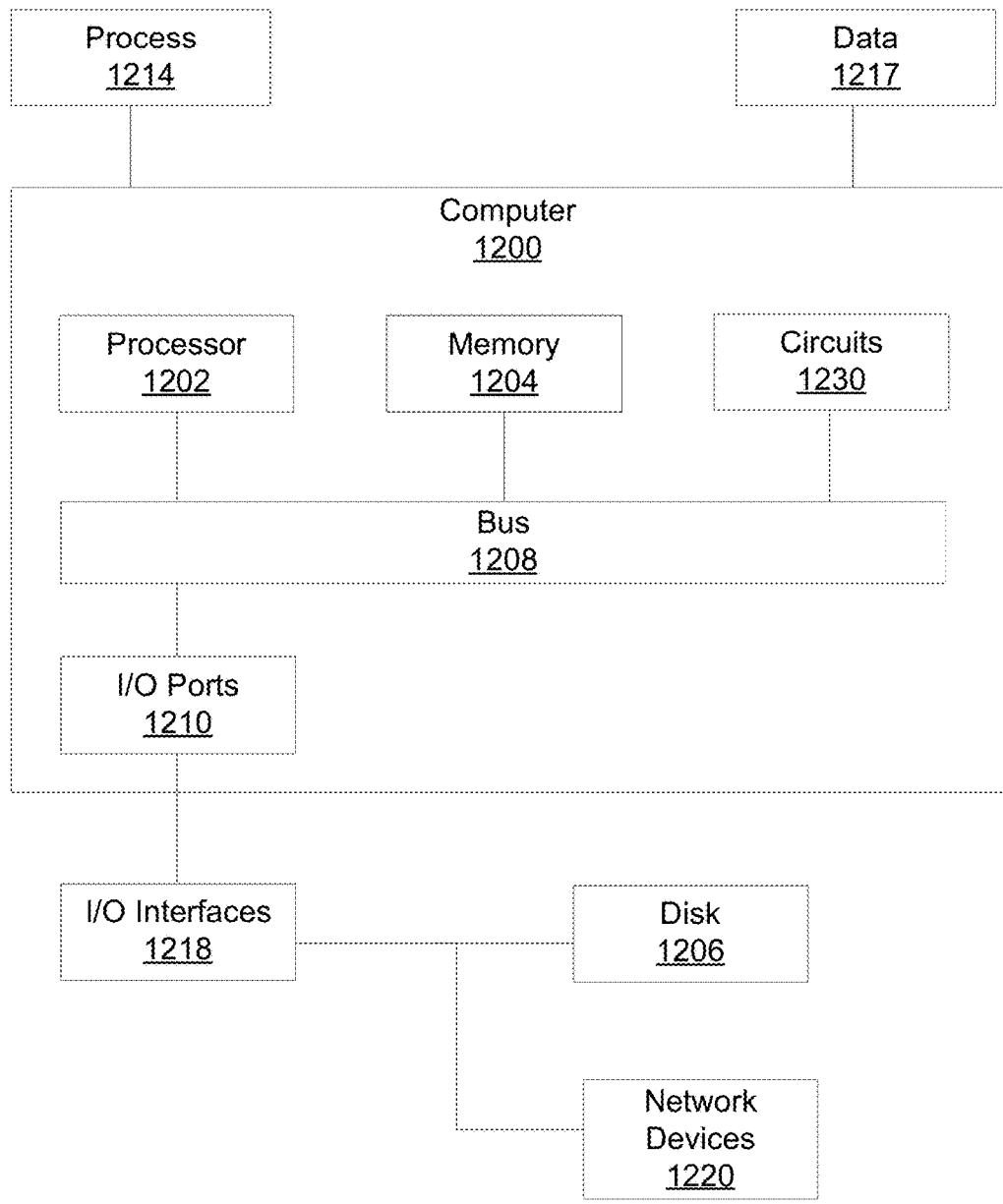
FIG. 12 illustrates an example computer in which embodiments described herein may operate.

FIG. 12 illustrates an example computer 1200 in which example methods illustrated herein can operate and in which example methods, apparatus, circuits, operations, or logics may be implemented. In different examples, computer 1200 may be part of a personalized medicine system, a post-TMT MPR prediction system, an MRI system, a digital whole slide scanner, a CT system, may be operably connectable to a post-TMT MPR prediction system, a CT system, an MRI system, a personalized medicine system, or a digital whole slide scanner, or may be part of a CADx system.

Computer 1200 includes a processor 1202, a memory 1204, and input/output (I/O) ports 1210 operably connected by a bus 1208. In one example, computer 1200 may include a set of logics or circuits 1230 that perform operations for or a method of NSCLC post-TMT MPR prediction using a machine learning classifier. Thus, the set of circuits 1230, whether implemented in computer 1200 as hardware, firmware, software, and/or a combination thereof may provide means (e.g., hardware, firmware, circuits) for predicting post-TMT MPR in NSCLC. In different examples, the set of circuits 1230 may be permanently and/or removably attached to computer 1200.

Processor 1202 can be a variety of various processors including dual microprocessor and other multi-processor architectures. Processor 1202 may be configured to perform operations or steps of methods claimed and described herein. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, or a memory stick. Furthermore, disk 1206 may include optical drives like a CD-ROM or a digital video ROM drive (DVD ROM). Memory 1204 can store processes 1214 or data 1217, for example. Data 1217 may, in one embodiment, include digitized CT imagery of tissue demonstrating NSCLC. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, circuits, logics, and peripherals using other buses that are not illustrated (e.g., PCIE, SATA, Infiniband, 794, USB, Ethernet).

Computer 1200 may interact with input/output devices via I/O interfaces 1218 and input/output ports 1210. Input/output devices can include, but are not limited to, CT systems, MRI systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network. Through the network, computer 1200 may be logically connected to remote computers. The networks with which computer 1200 may interact include, but are not limited to, a local area network (LAN), a wide area network (WAN), or other networks, including the cloud.

Examples herein can include subject matter such as an apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting post-TMT MPR or for generating a recommendation for post-TMT MPR, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media.

Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing instructions that when executed control a processor to perform operations for predicting major pathologic response (MPR) in non-small cell lung cancer (NSCLC), the operations comprising:
   accessing a baseline computed tomography (CT) image of a region of tissue (ROT) demonstrating NSCLC, the baseline CT image having a plurality of pixels, a pixel having an intensity;
   segmenting a tumoral region represented in the baseline CT image, the segmented tumoral region having a tumoral boundary;
   defining a peritumoral region by performing a morphological dilation of the tumoral boundary;
   extracting a set of tumoral radiomic features from the tumoral region;
   extracting a set of peritumoral radiomic features from the peritumoral region;
   extracting a set of clinico-pathologic features from the baseline CT image;
   providing the set of tumoral radiomic features, the set of peritumoral radiomic features, and the set of clinico-pathologic features to a machine learning classifier;
   receiving, from the machine learning classifier, a time-to-recurrence post-trimodality therapy (TMT) prediction, where the machine learning classifier computes the time-to-recurrence post-TMT prediction based on the set of tumoral radiomic features, the set of peritumoral radiomic features, and the set of clinico-pathologic features;
   generating a classification of the ROT as an MPR responder or MPR non-responder by classifying the ROT as an MPR responder or MPR non-responder based, at least in part, on the time-to-recurrence post TMT prediction; and
   displaying the classification.

2. The non-transitory computer-readable storage device of claim 1, where the set of tumoral radiomic features includes a tumoral Laplacian Law feature.

3. The non-transitory computer-readable storage device of claim 2, where the set of peritumoral radiomic features includes a peritumoral Laplacian Law feature.

4. The non-transitory computer-readable storage device of claim 3, where the set of clinico-pathologic features includes a lymphovascular invasion (LVI) status feature.

5. The non-transitory computer-readable storage device of claim 1, where the baseline CT image is a non-contrast, pre-neoadjuvant chemotherapy CT image of a region of tissue demonstrating stage III NSCLC.

6. The non-transitory computer-readable storage device of claim 1, where segmenting the tumoral region includes automatically segmenting the tumoral region using a region growing technique, thresholding, or a watershed approach.

7. The non-transitory computer-readable storage device of claim 1, where the peritumoral region is defined using a 15 mm morphological dilation of the tumoral boundary.

8. The non-transitory computer-readable storage device of claim 1, where the machine learning classifier is a multi-variable logistic regression (MLR) classifier trained using three-fold cross-validation on a training set of baseline CT images, where a member of the training set includes at least one baseline CT image of a region of tissue that experienced MPR post TMT, and at least one different baseline CT image of a region of tissue that did not experience MPR post TMT.

9. The non-transitory computer-readable storage device of claim of claim 1, where MPR is defined as less than or equal to ten percent viable tumor.

10. The non-transitory computer-readable storage device of claim 1, where classifying the ROT as an MPR responder or MPR non-responder includes classifying the ROT as an MPR responder or MPR non-responder with an area under the curve of at least 0.92.

11. The non-transitory computer-readable storage device of claim 1, the operations further comprising:
    upon determining that the classification is MPR responder:
       providing a recommendation of the ROT for TMT; and
       displaying the recommendation.

12. The non-transitory computer-readable storage device of claim 1, where the set of tumoral radiomic features includes an area of lesion feature and a Gabor feature;
    where the set of peritumoral radiomic features includes a Laws feature and a Law_Laplacian feature; and
    where the set of clinico-pathologic features includes a lymphovascular invasion (LVI) feature and a percent viable tumor feature.

13. The non-transitory computer-readable storage device of claim 1, where the set of tumoral radiomic features includes a Law_Laplacian W5×E5 feature;
    where the set of peritumoral radiomic features includes a Law_Laplacian S5×R5 feature, a Laws W5×S5 feature, and a Law_Laplacian W5×S5 feature;
    where the set of clinico-pathologic features includes a percent viable tumor feature; and
    where the machine learning classifier generates an overall survival (OS) prediction based, at least in part, on the set of tumoral radiomic features, the set of peritumoral radiomic features, and the set of clinico-pathologic features.

14. The non-transitory computer-readable storage device of claim 13, the operations further comprising displaying the OS prediction.

15. The non-transitory computer-readable storage device of claim 1, where the set of tumoral radiomic features includes a Law_Laplacian W5 by E5 feature;
    where the set of peritumoral radiomic features includes a Law_Laplacian W5 by S5 feature;
    where the set of clinico-pathologic features includes a lymphovascular invasion (LVI) status feature; and
    where the machine learning classifier generates a disease free survival (DFS) prediction based, at least in part, on the set of tumoral radiomic features, the set of peritumoral radiomic features, and the set of clinico-pathologic features.

16. The non-transitory computer-readable storage device of claim 15, the operations further comprising displaying the DFS prediction.

17. An apparatus for generating a recommendation that a patient receive trimodality therapy (TMT) for non-small cell lung cancer (NSCLC), the apparatus comprising:

a processor;

a memory configured to store a digitized baseline non-contrast computed tomography (CT) image of a region of tissue (ROT) demonstrating NSCLC;

an input/output (I/O) interface;

a set of circuits; and an interface that connects the processor, the memory, the I/O interface, and the set of circuits, the set of circuits comprising:

an image acquisition circuit configured to access a digitized baseline non-contrast CT image of an ROT demonstrating NSCLC, where the baseline CT image includes a tumoral region and a peritumoral region, the baseline CT image having a plurality of pixels, a pixel having an intensity;

a tumoral radiomics circuit configured to extract a set of tumoral radiomic features from the tumoral region, where the set of tumoral radiomic features includes an area of lesion feature and a Gabor feature;

a peritumoral radiomics circuit configured to extract a set of peritumoral radiomic features from the peritumoral region, where the set of peritumoral radiomic features includes a Laws feature and a Law_Laplacian feature;

a clinico-pathologic feature circuit configured to extract a set of clinico-pathologic features from the ROT, where the set of clinico-pathologic features includes a lymphovascular invasion (LVI) feature and a percent viable tumor feature;

a TMT recommendation circuit configured to:

generate a probability that the ROT will experience post-TMT major pathologic response (MPR) based on the set of tumoral features, the set of peritumoral features, and the set of clinico-pathologic features; and generate a recommendation for TMT based on the probability; and a display circuit configured to display the recommendation.

18. The apparatus of claim 17:

where the set of tumoral radiomic features includes a Law_Laplacian W5 by S5 feature;

where the set of peritumoral radiomic features includes a Laws W5 by S5 feature and a Law_Laplacian W5 by S5 feature;

where the set of clinico-pathologic features includes a percent viable tumor feature;

where the TMT recommendation circuit is further configured to:

to generate an overall survival (OS) prediction based on the set of tumoral features, the set of peritumoral features, and the set of clinico-pathologic features; and generate a recommendation for TMT based on the OS prediction; and where the display circuit is further configured to display the OS prediction.

19. The apparatus of claim 17:

where the set of tumoral radiomic features includes a Law_Laplacian W5 by E5 feature;

where the set of peritumoral radiomic features includes a Law_Laplacian W5 by S5 feature;

where the set of clinico-pathologic features includes a lymphovascular invasion (LVI) status feature, a histology feature, and a percentage of viable tumor feature;

where the TMT recommendation circuit is further configured to:

to generate a disease free survival (DFS) prediction based on the set of tumoral features, the set of peritumoral features, and the set of clinico-pathologic features; and generate a recommendation for TMT based on the DFS prediction; and where the display circuit is further configured to display the DFS prediction.

20. A non-transitory computer-readable storage device storing computer executable instructions that when executed by a computer control the computer to perform a method for predicting outcome of trimodality therapy (TMT), the method comprising:

accessing a pre-neoadjuvant chemotherapy, pre-surgery, baseline computed tomography (CT) image of a region of tissue demonstrating non-small cell lung cancer (NSCLC), the region of tissue including a tumor region and a peritumoral region, the baseline CT image having a plurality of pixels, a pixel having an intensity;

extracting a combined radiomic risk signature from the baseline CT image, where the combined radiomic risk signature includes at least one radiomic feature extracted from the tumoral region, at least one radiomic feature extracted from the peritumoral region, and at least one clinico-pathologic feature;

providing the combined radiomic risk signature to a machine learning classifier, where the machine learning classifier computes a major pathologic response (MPR) prediction based on the combined radiomic risk signature, computing a risk score based on the combined radiomic risk signature, that is predictive of a high risk or low risk of disease free survival (DFS) and generating a DFS prediction based on the risk score, or generating an overall survival (OS) prediction based on the combined radiomic risk signature;

receiving, from the machine learning classifier, the MPR prediction;

generating a TMT outcome prediction based on the MPR prediction, the DFS prediction, or the OS prediction; and displaying the TMT outcome prediction and at least one of the MPR prediction, the DFS prediction, or the OS prediction.

* * * * *

UNITED STATES PATENT AND TRADEMARK OFFICE
CERTIFICATE OF CORRECTION

| | | |
|---|---|---|
| PATENT NO. | : 10,441,225 B2 | Page 1 of 1 |
| APPLICATION NO. | : 16/236675 | |
| DATED | : October 15, 2019 | |
| INVENTOR(S) | : Anant Madabhushi et al. | |

It is certified that error appears in the above-identified patent and that said Letters Patent is hereby corrected as shown below:

In the Specification

Column 1, Lines 17 through 24; please replace "This invention was made with government support under grants 1U24CA199374-01, R01 CA202752-01 A1, R01 CA208236-01 A1, R21 CA216579-01 A1, R21CA195152-01, R01DK098503-02, and 1 C06 RR012463-01 awarded by the National Institutes of Health. Also grants W81XWH-13-1-0418 and W81XWH-14-1-0323, W81XWH-16-1-0329 awarded by the Department of Defense. The government has certain rights in the invention." with -- This invention was made with government support under grants CA199374, DK098503, CA202752, RR012463, CA208236, CA195152, and CA216579 awarded by the National Institutes of Health; and grant(s) W81XWH-13-1-0418, W81XWH-14-1-0323, and W81XWH-16-1-0329 awarded by the Department of Defense. The government has certain rights in the invention. --

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*